US008650973B2

(12) United States Patent
Wei et al.

(10) Patent No.: US 8,650,973 B2
(45) Date of Patent: Feb. 18, 2014

(54) DILUTER FOR MEASURING ENGINE EXHAUST EMISSIONS

(75) Inventors: Qiang Wei, San Antonio, TX (US); Imad Said Abdul-Khalek, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 290 days.

(21) Appl. No.: 13/305,947

(22) Filed: Nov. 29, 2011

(65) Prior Publication Data

US 2013/0133440 A1 May 30, 2013

(51) Int. Cl.
*G01N 1/22* (2006.01)

(52) U.S. Cl.
USPC ........................................ 73/863.03

(58) Field of Classification Search
None
See application file for complete search history.

(56) References Cited

U.S. PATENT DOCUMENTS 7,201,071 B2 4/2007 Wei et al.

*Primary Examiner* — Robert R Raevis

(74) *Attorney, Agent, or Firm* — Chowdhury & Georgakis PC; Ann C. Livingston

(57) ABSTRACT

A diluter for diluting a sample flow of a test gas to allow subsequent measurement of emissions in the test gas. During a calibration mode, a first flow control element receives and controls the dilution flow, a second flow control element receives and measures only the dilution flow, and a third flow control element is closed. Also during calibration, the second flow control element is calibrated to the first flow control element. During a measurement mode, the same dilution flow rate is maintained in the first and second flow control elements, the sample flow and dilution flow are mixed, and the mixed flow flows into both the second flow control element and the third flow control element. Also during measurement, the third flow control element controls sample flow, and the second flow control element delivers a portion of the mixed flow to the instrument.

14 Claims, 2 Drawing Sheets

DILUTER FOR MEASURING ENGINE EXHAUST EMISSIONS

TECHNICAL FIELD OF THE INVENTION

The invention relates to diluting engine exhaust or other gases that contain small particles so that emissions can be measured.

BACKGROUND OF THE INVENTION

In order to measure and characterize engine exhaust particulate matter (PM) emissions, it is required that the engine exhaust be diluted. More specifically, because the exhaust contains a high concentration of particles, the measurement sample must be diluted (mixed with dilution air) with a high dilution ratio (typically greater than 100:1) to reach the measurable range of particle number instruments. Once the measurement is made from the mixture, the dilution ratio can be used to determine the actual particle concentration in the sample.

In addition to providing high dilution ratios, an emissions measurement system should provide a wide range of ratios. Due to the variety of engine technologies and operating conditions, the concentration of engine exhaust particles may vary widely. To obtain accurate measurement results, wide range dilution capability is required.

One approach to particle measurement is to use a partial flow diluter that controls dilution air flow and total mixture flow with mass flow controllers. The sample flow is calculated by subtracting the dilution air flow from the total mixture flow. Then, the dilution ratio is calculated by dividing the total mixture flow by the calculated sample flow. At low dilution conditions, this approach provides an accurate dilution ratio calculation. However, as the dilution ratio increases, the accuracy of the calculated dilution ratio suffers due to uncertainties of the total flow and dilution air flow measurements. This results in inaccurate characterizations of exhaust emissions.

For emissions measurements at higher dilution ratios, ejector diluters have been used. However, ejector diluters tend to have a narrow dilution ratio range, and have other shortcomings.

Rotating disk diluters permit a wide range of dilution ratios, but tend to exhibit dilution ratio drift and other shortcomings.

U.S. Pat. No. 7,201,071, to Wei, et al, describes a wide range continuous diluter. A flow meter in the sample line directly measures the sample flow without causing particle losses.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The following description is directed to a diluter for diluting engine exhaust to desired constant dilution ratios. It provides real-time and accurate dilution ratios, as well as a wide dilution ratio range without causing engine exhaust particle losses.

As indicated in the Background, a typical application of the diluter is dilution of engine exhaust for exhaust emissions (particle and/or gaseous) measurement. The diluter can be built either as a standalone system, or it can be integrated with an exhaust emissions measurement system.

Figure 1:
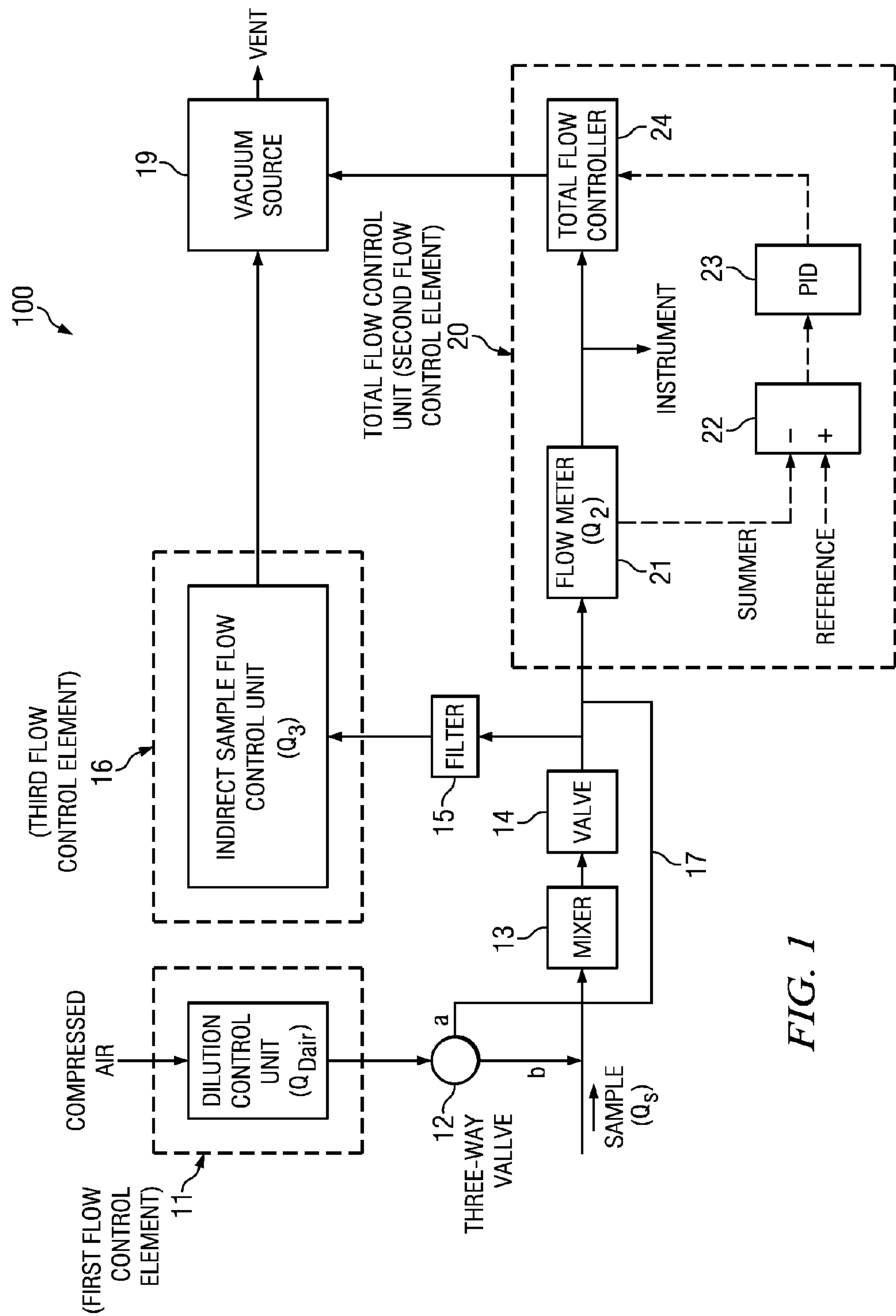
FIG. 1 is a schematic diagram of the diluter, also showing its three flow control elements.

FIG. 1 is a schematic diagram of a diluter 100 in accordance with the invention. The main elements of diluter 100 are a dilution control system 11, a three-way valve 12, a mixer 13, a valve 14, a filter 15, a indirect sample flow control unit 16, a vacuum source 19, and a total flow control unit 20 having a flow meter 21, a summer 22, a Proportional-Integral-Derivative (PID) controller 23, and a total flow controller 24.

The inlet for the exhaust sample flow is into mixer 13. The outlet to the emissions measurement instrument is between flow meter 21 and total flow controller 24.

Diluter 100 may be understood as having three flow control elements, identified as 11, 16, and 20. The dilution control unit 11 is a first flow control element. The total flow control unit 20 (flow meter 21, the flow outlet to the instrument, and the total flow controller 24) is a second flow control element. The indirect sample control unit 16 is a third flow control element.

The first flow control element (the dilution control unit 11) controls and measures the dilution flow into diluter 100. Typically, and in the example of this description, the dilution gas is air. It may be a mass flow controller or other flow control device with good flow control and measurement accuracy. It supplies dilution air into the diluter 100 by connecting to a particle-free compressed air source.

The second flow control element (flow meter 21, total flow controller 24 and the outlet to instrument) uses flow meter 21 to measure flow without causing particle loss. An example of a suitable flow meter 21 is a venturi flow meter or an orifice flow meter.

The outlet to instrument located downstream of flow meter 21 supplies flow to the measurement instrument. Generally, this flow is constant (although it can be varied). To maintain the flow through the second flow control unit 20 at a desired value, the total flow controller 24 and the PID controller 23 manage the flow through the flow meter 21 by comparing flow through flow meter 21 to a reference value in summer 22. This produces an error signal used by PID controller 23 to provide a control signal for total flow controller 24. If the measured value is higher than the reference, the PID controller 23 drives controller 24 to reduce the flow. If the measured value is less than the reference value, the PID controller 23 drives controller 24 to increase the flow. In other embodiments, feedback control loops having elements other than summer 22 and PID controller 23 may be possible.

The third flow control element (indirect sample flow control unit 16) is located downstream of filter 15. An example of a suitable filter 15 is a High Efficiency Particle Air (HEPA) filter. Filter 15 removes particles from the flow and protects indirect sample flow control unit 16 from particle contamination.

The outlet of indirect sample flow control unit 16 is connected to vacuum source 19, which draws flow through the diluter 100. As explained below, indirect sample flow control unit 16 measures and controls flow at a desired value precisely. With different applications and requirements for the accuracy of the dilution ratio, unit 16 can include either a single flow measuring and control device or multiple flow measuring and control devices.

As explained below, by controlling dilution air flow in the first flow control element 11 and the total mixture flow in the second flow control element 20 at the same flow rate, the sample flow rate is the same as the flow through the third flow control element 16. Because flow in the third flow control element 16 is controlled and measured accurately, the sample flow rate is controlled and measured by the third flow element 16 indirectly. By changing the flow through the third flow control element 16, the sample flow is changed.

There are at least two approaches to adjusting the dilution ratio provided by dilutor 100. One approach is to control the flow through the third flow control element 16 when the dilution air flow has no change. An alternative approach is to change the dilution air flow rate through the first flow control element 11. By controlling either the sample flow or the dilution air flow, the dilution ratio is controlled.

As stated above, the third flow control element 16 may have either a single flow meter or several flow meters. To obtain precise dilution ratios from diluter 100 in a wide dilution ratio range, a single flow meter may not be able to measure the flow accurately through the whole range. In this case, multiple flow meters in the third flow control element 16 can provide accurate flow measurement. Each flow meter can be used to provide accurate flow measurement in a specific range. When the dilution ratio is controlled in the range for that flow meter, a control loop in the third flow control element 16 activates the flow control loop for that flow meter.

Equation 1 below defines the dilution ratio, DR, in diluter 100. The value $Q_{Dair}$ is the dilution air flow rate at a standard or a reference condition, and $Q_S$ is the sample flow rate at a standard or a reference condition.

$$DR = \frac{Q_{Dair} + Q_S}{Q_S} = 1 + \frac{Q_{Dair}}{Q_S} \quad \text{(Equation 1)}$$

Figure 3:
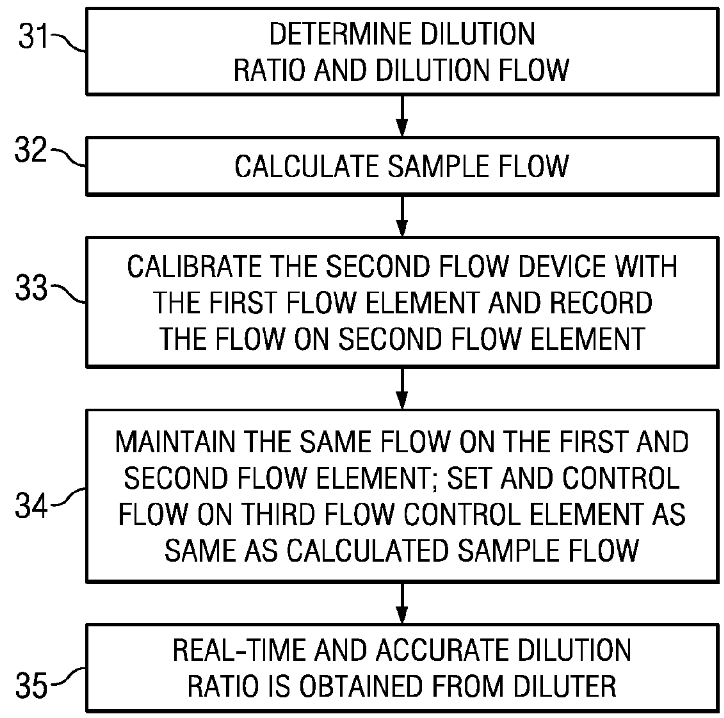
FIG. 3 illustrates a method of using a diluter having three flow control elements to provide a range of dilution ratios.

FIG. 3 illustrates operation of diluter 100. In Step 31, at the beginning of operation, the dilution air flow and dilution ratio are determined. Then, in Step 32, the sample flow, taken from the engine exhaust system, can be calculated from Equation 1.

Step 33 is referred to herein as a "calibration mode" of the diluter. In Step 33, the second flow control element 20 is calibrated to the first flow control element 11. To perform this step, three-way (a one-to-two multiplexer) valve 12 switches flow to point a. An example of a suitable three-way valve is a solenoid valve. This results in bypassing mixer 13 and valve 14 via bypass line 17. The third flow control element 16 is shut off (closed) so that no flow moves through it. Valve 14, upstream of filter 17, is closed to stop the sample flow from moving into the second flow control element 20 during calibration.

Figure 2:
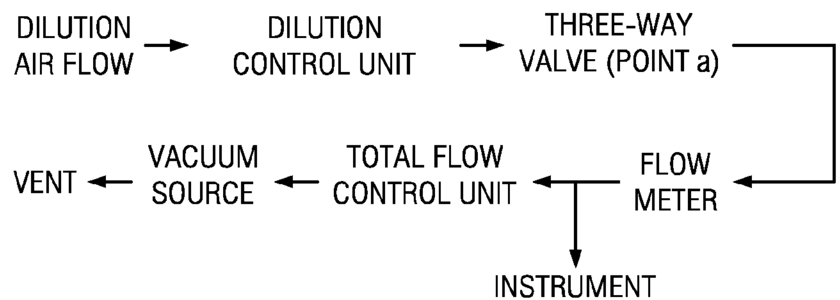
FIG. 2 illustrates the flow through the diluter during the calibration mode.

FIG. 2 presents flow routes for the calibration step (Step 33). Because the whole dilution air flow, measured and controlled by the first flow control element 11, flows through flow meter 21 in the second flow control element 20, the flow measured by flow meter 21 should be the same as the flow measured by the first flow control element 11.

If, due to errors of the first flow control element 11 and/or flow meter 21, their measured flows are slightly different, there are at least two approaches to handle this difference. The first approach is to generate a coefficient from the calibration to correct both flows to the same number. The second approach is to keep both flows with no change.

In the embodiment of this description, the use of the second approach is assumed. With the second approach, the actual flow measured by flow meter 21 is recorded after the system is stabilized. The recorded value is used as a set point for subsequent operation of total flow control unit 20.

Downstream of flow meter 21, a fraction of flow moves into the measurement instrument. The rest of the flow moves through the total flow control unit 20. To make the pressure in the diluter 100 similar to the actual operation of the diluter in the calibration step, the total flow control unit 20 is adjusted to make the flow pressure at the inlet of flow meter 21 close to the ambient air pressure.

At the completion of the calibration step (Step 33), the "measurement mode" (Step 34) is started. The three-way valve 12 is switched to point b, and valve 14 is opened. In Step 34, the dilution control unit 11 maintains the dilution flow the same as in Step 33. The flow moving through flow meter 21 is controlled to the same value recorded in Step 33 by PID controller 21. The reference value for the flow control is that measured and recorded in Step 33.

While the flow through the second flow control element 20 is maintained at the flow recorded in Step 33, the dilution flow controlled by the first flow control element 11 equals the flow through the second flow control element 20.

The following equation expresses the flow balance in the diluter 100, where $Q_2$ is the flow measured and controlled by the second flow control element 20 at a standard or a reference condition and $Q_3$ is the flow moving through the third flow control element 16 at a standard or a reference condition.

$$Q_{Dair} + Q_S = Q_2 + Q_3 \quad \text{(Equation 2)}$$

Because the flow in the second flow element 20 is controlled to be the same as in the first flow control element 11, Equation 2 can be rewritten as:

$$Q_S = Q_3 \quad \text{(Equation 3)}$$

It can be observed from Equation 3 that the sample flow ($Q_S$) equals the flow ($Q_3$) through the third flow control element 16. Thus, the third flow control element 16 measures and controls the sample flow indirectly. By changing the flow rate on the third flow control element 16, the sample flow is changed.

Before the start of Step 33, the dilution ratio and the dilution air flow are determined. The sample flow for engine exhaust can be calculated from Equation 1. To obtain the desired dilution ratio, the sample flow rate calculated from Equation 1 is used as the flow set point for the third flow control element 16. To change the dilution ratio of the diluter 100, the set point on the third flow control element 16 is changed. An alternative approach to control the dilution ratio is using a different dilution air flow than used in Step 33.

For some applications, very wide range and accurate dilution ratios may be required. It is possible that the third flow control element 16 may not provide the accuracy required through the entire range. In this case, multiple flow measurement and control devices can be integrated to provide the accuracy and flow ranges required, depending on the application. This procedure can be operated manually or automatically.

In Step 34, the sample flow moves into diluter 100 through the sample inlet. It mixes with the dilution air flow uniformly in mixer 13. The mixed flow then moves through valve 14 without losing particles because there is no flow restriction in valve 14 while it is open. Downstream of valve 14, a portion of the flow, which has the same flow rate as the sample flow, passes through filter 15 and then moves into the third flow control element 16. Filter 15 protects the third flow control element 16 from particle contamination.

At the same time, another portion of the mixed (sample/dilution) flow from mixer 13 flows through the second flow control element 20. This flow is controlled with the total flow controller 24 to the desired flow rate. Upstream of the total flow controller 24, but downstream of flow meter 21, some fraction of flow moves into the measurement instrument. Due to real-time dilution air flow and the sample flow being measured by the diluter 100, the real-time dilution ratio can be made available.

What is claimed is:

1. A diluter for diluting a sample flow of test gas to allow subsequent measurement of emissions contained in the test gas with an instrument, comprising:

a dilution control unit for receiving and controlling a dilution flow into the diluter at a controlled dilution flow rate;

a sample gas inlet for receiving the sample flow;

a mixer connected to the dilution control unit and to the sample gas inlet for receiving and mixing the dilution flow and sample flow to provide a mixed flow;

a bypass line for carrying the dilution flow around the mixer during a calibration mode of the diluter;

a valve for directing the dilution flow into the mixer or into the bypass line;

a vacuum source for pulling flow through the diluter;

an indirect sample flow control unit downstream the mixer, operable to indirectly control the sample flow rate during a measurement phase of the diluter;

a total flow control unit downstream the mixer, operable to receive and measure only the dilution flow from the bypass line, during a calibration mode of the diluter;

the total flow control unit further operable to control the mixed flow at a controlled flow rate and deliver a portion of the mixed flow to the instrument, during a measurement mode of the diluter.

2. The diluter of claim 1, wherein the total flow control unit has a flow meter downstream the mixer, a flow controller connected to the vacuum source, and a control loop.

3. The diluter of claim 2, wherein the control loop uses proportional/integral/derivative control.

4. The diluter of claim 2, wherein the flow meter is a venturi flow meter or an orifice flow meter.

5. The diluter of claim 2, further comprising an outlet to the instrument between the flow meter and the flow controller.

6. The diluter of claim 1, wherein the dilution control unit is a mass flow controller.

7. The diluter of claim 1, further comprising a filter between the mixer and the indirect sample flow control unit.

8. The diluter of claim 1, wherein the total flow control unit has multiple flow meters, having different flow measurement ranges.

9. A method of using a diluter for diluting a sample flow of a test gas to allow subsequent measurement of emissions contained in the test gas with an instrument, comprising:

providing a diluter having at least three flow control elements, namely a first flow control element, a second flow control element, and a third flow control element;

wherein the first flow control element is a dilution control unit upstream a mixer, the second flow control element is a total flow control unit downstream the mixer, and the third flow control element is an indirect sample flow control unit downstream the mixer;

calculating a sample flow rate from a known dilution ratio and dilution air flow rate;

during a calibration mode, using the first flow control element to receive and control the dilution flow, using the second flow control element to receive and measure only the dilution flow, and closing the third flow control element;

further during the calibration mode, calibrating the second flow control element to the first flow control element;

during a measurement mode, maintaining the controlled dilution flow rate in the first and second flow control element, receiving the sample flow and the dilution flow into the mixer, receiving the mixed flow into the second flow control element and the third flow control element, using the third flow control element to control flow at the calculated sample flow rate, and delivering a portion of the mixed flow to the instrument.

10. The method of claim 9, further comprising adjusting the dilution ratio by adjusting the flow through the indirect sample flow control unit.

11. The method of claim 9, further comprising adjusting the dilution ratio by adjusting the flow through the dilution flow control unit.

12. The method of claim 9, wherein the third flow control element comprises multiple flow meters with different measurement ranges.

13. The method of claim 9, wherein the second flow control element has a flow meter downstream the mixer, a flow controller connected to the vacuum source, and a control loop.

14. The method of claim 9, wherein the step of delivering a portion of the mixed flow to the instrument is performed within the second flow control element.

* * * * *